US008861822B2

(12) United States Patent  
Pagoulatos et al.

(10) Patent No.: US 8,861,822 B2
(45) Date of Patent: Oct. 14, 2014

(54) SYSTEMS AND METHODS FOR ENHANCED IMAGING OF OBJECTS WITHIN AN IMAGE

(75) Inventors: Nikolaos Pagoulatos, Bothell, WA (US); Qinglin Ma, Woodinville, WA (US); Andrew K. Lundberg, Woodinville, WA (US); Richard Hippe, Snohomish, WA (US); Clinton T. Siedenburg, Everett, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 466 days.

(21) Appl. No.: 12/790,109

(22) Filed: May 28, 2010

(65) Prior Publication Data

US 2011/0249878 A1  Oct. 13, 2011

Related U.S. Application Data

(60) Provisional application No. 61/321,666, filed on Apr. 7, 2010.

(51) Int. Cl.
| | | |
|---|---|---|
| G06K 9/00 | (2006.01) | |
| G06K 9/36 | (2006.01) | |
| G06T 5/50 | (2006.01) | |
| G01S 15/89 | (2006.01) | |
| A61B 8/08 | (2006.01) | |
| A61B 19/00 | (2006.01) | |

(52) U.S. Cl.
CPC ............... *A61B 8/0841* (2013.01); *G06T 5/50* (2013.01); *G06T 2207/10132* (2013.01); *G01S 15/8995* (2013.01); *G06T 2207/20221* (2013.01); *A61B 19/5244* (2013.01)
USPC .......................................... 382/131; 382/284

(58) Field of Classification Search
CPC ................ A61B 19/5244; A61B 2019/5276; A61B 8/0841; G01S 15/8995; G06T 5/50; G06T 2207/20221; G06T 2207/10132

USPC ................... 382/131, 284; 600/461, 443
See application file for complete search history.

(56) References Cited

U.S. PATENT DOCUMENTS 6,048,312 A * 4/2000 Ishrak et al. .................. 600/443
6,790,181 B2 * 9/2004 Cai et al. ....................... 600/443
(Continued)

FOREIGN PATENT DOCUMENTS

WO   WO-2011127191 A1   10/2011

OTHER PUBLICATIONS

Ding, Mingyue, and Aaron Fenster. "A real-time biopsy needle segmentation technique using Hough transform." Medical Physics 30 (2003): 2222.*

(Continued)

*Primary Examiner* — John Pauls
*Assistant Examiner* — Jonathan Durant
(74) *Attorney, Agent, or Firm* — Perkins Coie LLP

(57) ABSTRACT

Systems and methods which implement a plurality of different imaging signatures in generating an image frame are shown. A first imaging signature may be configured for providing relatively high quality images with respect to subsurface regions of living tissue, for example, whereas a second imaging signature may be configured for providing relatively high quality images with respect to interventional instruments inserted into living tissue at a steep angle. Image sub-frames generated using each such different imaging signature are blended to form a frame of the final image providing a relatively high quality image of various objects within the volume being imaged.

10 Claims, 6 Drawing Sheets

(56) References Cited

U.S. PATENT DOCUMENTS

| | | | |
|---|---|---|---|
| 6,911,008 B2 * | 6/2005 | Pelissier et al. | 600/443 |
| 6,951,542 B2 * | 10/2005 | Greppi et al. | 600/443 |
| 7,270,634 B2 * | 9/2007 | Scampini et al. | 600/447 |
| 7,338,448 B2 * | 3/2008 | Hao et al. | 600/443 |
| 7,346,228 B2 * | 3/2008 | Sabourin et al. | 382/284 |
| 8,088,071 B2 | 1/2012 | Hwang et al. | |
| 8,147,408 B2 | 4/2012 | Bunce et al. | |
| 2002/0173719 A1 * | 11/2002 | Zhao et al. | 600/437 |
| 2003/0135119 A1 * | 7/2003 | Lee et al. | 600/461 |
| 2005/0008254 A1 * | 1/2005 | Ouchi et al. | 382/284 |
| 2008/0077009 A1 * | 3/2008 | Lee et al. | 600/437 |
| 2008/0183079 A1 | 7/2008 | Lundberg | |

OTHER PUBLICATIONS

William A. Barrett and Alan S. Cheney. 2002. Object-based image editing. ACM Trans. Graph. 21, 3 (Jul. 2002), 777-784.*

Smith, Alvy Ray. Image compositing fundamentals. Technical Memo 4, Microsoft Corporation, 1995.*

Wilhjelm, Jens E., et al. "Influence of insonification angle on echogenicity of B-mode images of atherosclerotic plaque in vitro." Ultrasonics Symposium, 1998. Proceedings., 1998 IEEE. vol. 2. IEEE, 1998.*

Entrekin, R., et al. "Real time spatial compound imaging in breast ultrasound: technology and early clinical experience." medicamundi 43.3 (1999): 35-43.*

Hansen, Christian, et al. "An automated system for full angle spatial compounding in ultrasound breast imaging." 4th European Conference of the International Federation for Medical and Biological Engineering. Springer Berlin Heidelberg, 2009.*

Rohling, Robert, Andrew Gee, and Laurence Berman. "Three-dimensional spatial compounding of ultrasound images." Medical Image Analysis 1.3 (1997): 177-193.*

Jespersen SK, Wilhjelm JE & Sillesen H: Ultrasound Spatial Compound Scanner for Improved Visualization in Vascular Imaging. 1998 IEEE Int. Ultrasonic Symp., Sendai, Miyagi, Japan. 1998.*

International Search Report and Written Opinion issued Jun. 21, 2011 for International Application No. PCT/US2011/031447, 9 pages.

* cited by examiner

SYSTEMS AND METHODS FOR ENHANCED IMAGING OF OBJECTS WITHIN AN IMAGE

REFERENCE TO RELATED APPLICATIONS

The present application claims priority to U.S. Provisional Patent Application Ser. No. 61/321,666, entitled "Systems and Methods for Enhanced Imaging of Objects Within An Image", filed Apr. 7, 2010, and is related to co-pending and commonly assigned U.S. patent application Ser. No. 11/749,319 entitled "System and Method for Optimized Spatio-Temporal Sampling," filed May 16, 2007, and Ser. No. 11/854,371 entitled "System and Method for Spatial Compounding Using Phased Arrays," filed Sep. 12, 2007, the disclosures of which are hereby incorporated herein by reference.

TECHNICAL FIELD

The invention relates generally to ultrasound imaging and, more particularly, to enhancing the visualization of objects within an image.

BACKGROUND OF THE INVENTION

Ultrasound imaging systems have gained wide acceptance for use in providing images of objects and areas which are not otherwise visible to an observer. Such ultrasound imaging systems are typically configured with various imaging parameters selected to produce the best overall ultrasound image quality and not the best visualization of individual objects that may be present in a volume being imaged. As a result, the visualization of individual objects is typically compromised to achieve an overall satisfactory ultrasound image quality.

Objects visualized and represented in ultrasound images may comprise biological structures, such as human tissue and organs, and man-made structures such as implantable devices, instruments, etc. The various biological and man-made structures may require specific imaging parameters to achieve high quality ultrasound visualization of the structures that are different from parameters selected to achieve overall image quality. In addition, the imaging parameters chosen to achieve high quality visualization of one type structure may be significantly different than the parameters chosen to achieve high quality visualization of a different type of structure. Thus, it is not a simple task to provide high quality visualization of one or more individual objects within an overall high quality ultrasound image.

It is now common practice to use ultrasound imaging systems to aid in the guidance and placement of man-made instruments and other objects. For example, interventional instruments, such as needles, catheters, etc., may be used to deliver medication or other fluids directly into a nerve, an artery, or a vein deep within or internal to a patient's body. Such procedures may require precise positioning of an instrument internal to a patient thus requiring high quality ultrasound visualization of both biological structures and man-made instruments.

Using ultrasound imaging systems configured with imaging parameters selected to optimize overall image quality, it is often difficult, and sometimes impossible, to provide adequate visualization of instruments inserted at a steep angle with respect to an ultrasound transducer used to generate an ultrasound image. The problem of poor visualization of instruments inserted at steep angles results, at least in part, from the fact that representations of such instruments in ultrasound images are based on ultrasound echoes that are reflected from the instruments in a specular fashion. The principles of specular reflection indicate that for steep insertion angles the ultrasound echoes reflected from the instruments do not sufficiently intersect the ultrasound transducer elements to produce a clear representation of the instrument in the resulting ultrasound image.

Due to the generally poor representation in ultrasound images of instruments inserted at steep angles, a clinician must often rely on secondary artifacts to visualize or "guess" where the interventional instrument is within a volume (e.g., within a patient's anatomy). For example, a clinician may rely upon movement of tissue, or other structures visible within the resulting image, caused by pressure from a needle as the needle is inserted or otherwise moved, to visualize where the needle is within the patient's anatomy. Visualization of the location of an interventional instrument based upon the movement of nearby structures generally does not provide for precise location determinations.

Another technique used for visualizing the location of an interventional instrument requires injecting fluid through the interventional instrument and observing the resulting image as the fluid moves through the media of the volume being imaged (e.g., as the fluid moves into and through tissue). This technique thus also relies on secondary artifacts and has not been found to be particularly satisfactory.

Several specially-designed echogenic needles have been introduced to address the problem of poor visualization of instruments inserted at steep angles. These specialty needles are typically designed and constructed in a way that the ultrasound waves reflected from the needle reach the ultrasound transducer elements even when the needle is inserted at steep angles. However, there are a number of factors that reduce the effectiveness and desirability of such needles. For example, the increased cost associated with such special needles reduces their clinical acceptance and widespread use.

BRIEF SUMMARY OF THE INVENTION

The present invention is directed to systems and methods providing ultrasound imaging signatures for generating ultrasound images. For example, a plurality of ultrasound imaging signatures, wherein each imaging signature is related to an object in an imaged volume, may be utilized according to embodiments of the invention. Using such ultrasound imaging signatures, an ultrasound imaging system may provide improved or optimized imaging of various objects in the imaged volume.

According to embodiments of the present invention, an ultrasound imaging signature comprises one or more ultrasound imaging parameter values, where each imaging parameter is associated with either the acquisition or processing of ultrasound data. Each imaging signature of a plurality of imaging signatures may be associated with the same ultrasound modality, e.g., B-mode, color-flow, power-doppler, elastography and others. Moreover, each ultrasound imaging signature of embodiments has one or more imaging parameters set at values tailored to the high quality ultrasound visualization of a particular object of interest.

The ultrasound imaging signatures of embodiments of the invention are optimized or otherwise configured for imaging particular objects, structures, aspects, etc. of a volume being imaged. For example, a first imaging signature may be configured for providing relatively high quality images with respect to subsurface regions of living tissue (e.g., general patient anatomy), whereas a second imaging signature may be configured for providing relatively high quality images with respect to interventional instruments (e.g., a needle) inserted into living tissue at a steep angle.

Sub-frames generated using different ones of such ultrasound imaging signatures are preferably combined to form a frame providing a relatively high quality image of the various structures, attributes, aspects, etc., collectively referred to as objects (e.g., general patient anatomy and interventional instrument) within the volume being imaged. Frames formed according to embodiments are preferably combined or blended to form a final image.

According to a preferred embodiment, two ultrasound imaging signatures are used wherein one ultrasound imaging signature is tailored to provide high image quality for human tissues and another is tailored to provide high image quality for interventional instruments such as needles inserted at steep insertion angles. According to aspects of the embodiments, an ultrasound imaging signature of the foregoing two ultrasound imaging signatures comprises a predetermined set of steering angles specifically targeted for high quality interventional instrument visualization at steep insertion angles. According to other aspects of the embodiments, one or more ultrasound imaging parameter values are changed between the two ultrasound imaging signatures, where the one or more ultrasound parameters include transmit waveform, ratio of transmit to receive beamformed lines, steering angle, receive line density, number of focal zones, location of focal zones, quadrature bandpass filter type and coefficients, compression curve, speckle reduction parameters, etc.

Other embodiments of the invention operate to identify an area or block of interest within a frame for combining or blending with one or more other frames to form a final image. For example, a block in which an interventional instrument is to be disposed may be known or determined. Thus, embodiments of the invention may crop, or otherwise render insignificant, portions outside of the block prior to blending an interventional instrument frame with an anatomical structure frame when forming a final image. Such embodiments may be utilized in mitigating or avoiding image clutter, artifacts, etc. associated with the use of an interventional instrument imaging signature.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1A:
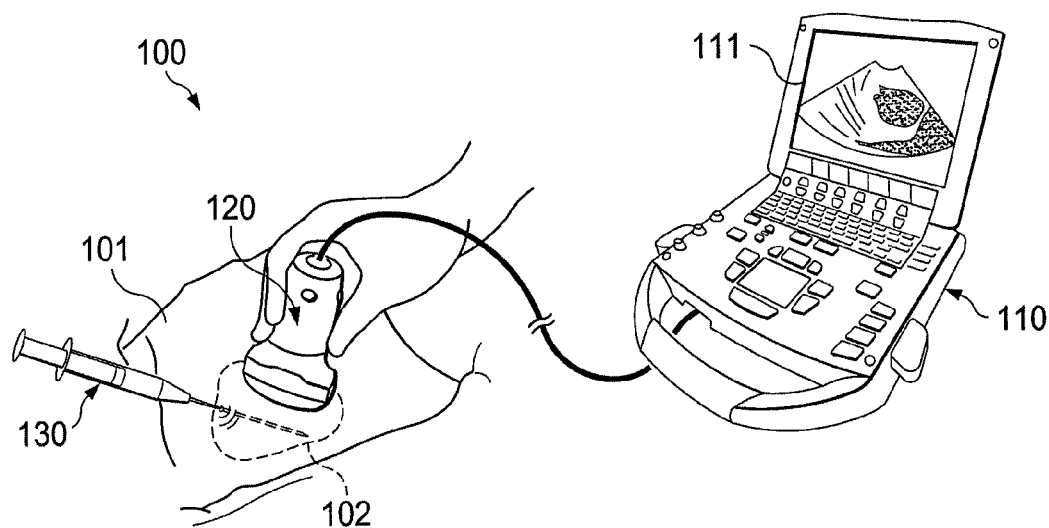
FIGS. 1A and 1B show an embodiment of an ultrasound imaging system adapted according to an embodiment of the invention.

FIG. 1A shows an ultrasound imaging system adapted according to an embodiment of the invention. Specifically, ultrasound imaging system 100 is shown comprising system unit 110 coupled to transducer 120. System unit 110 of embodiments comprises a processor-based system operable to control transducer 120 to transmit and receive ultrasound signals, to process the received ultrasound signals, to generate an image using the processed received ultrasound signals, and to display the generated image (e.g., on display 111). Transducer 120 comprises an array of ultrasound elements operable to controllably transmit and receive ultrasound signals. Detail with respect to imaging systems which may be adapted according to the concepts of the present invention is provided in co-pending and commonly assigned U.S. patent application Ser. No. 12/467,899 entitled "Modular Apparatus for Diagnostic Ultrasound," the disclosure of which is hereby incorporated herein by reference.

In operation, ultrasound imaging system 100 implements an imaging technique known as "spatial compounding" wherein a number of different signal steering angles are used to illuminate a volume being imaged. Additional detail regarding spatial compounding techniques is found in the above referenced patent applications entitled "System and Method for Optimized Spatio-Temporal Sampling" and "System and Method for Spatial Compounding Using Phased Arrays." Using typical spatial compounding techniques, the data collected with respect to an imaged volume using a single steering angle are processed to form a sub-frame and all the sub-frames of the imaged volume are then compounded to produce a frame. A frame may be formed, for example, using two sub-frames, three sub-frames, four sub-frames or more, corresponding to the use of two, three, four or more steering angles respectively.

FIGS. 2A-2D illustrate the use of three sub-frames in generating a frame. Frame 200 of FIG. 2D, for example, illustrates a top-down view into volume being imaged 101, such as may comprise living tissue of a patient's anatomy. In the illustrated example, frame 200 of FIG. 2D may be generated by ultrasound imaging system 100 using sub-frames 201-203 of FIGS. 2A-2C. Sub-frame 201 of the illustrated embodiment implements a straight down view (e.g., a steering angle of 0°) with respect to transducer 120 and provides sub-frame data for the un-steered sub-frame. Sub-frames 202 and 203 of the illustrated embodiment implement offset steering angles. For example, the steering angle for sub-frame 202 may be directed to the left at approximately −14° and the steering angle for sub-frame 203 may be directed to the right at approximately +14°. The data provided by these sub-frames is compounded to generate frame 200 having improved image characteristics over a frame generated using a single steering angle (e.g., a frame based solely on the data available for sub-frame 201). The resulting frame 200 produces a desired higher image quality by, for example, mitigating effects of shadowing, reducing speckle noise, and improving boundary delineation.

Ultrasound imaging systems employing spatial compounding are typically configured with various imaging parameters selected to produce the best overall ultrasound image quality and not the best visualization of individual objects within a volume being imaged. In general, the term "imaging parameters" refers to parameters associated with either the acquisition or processing, or both, of ultrasound data. Examples of such imaging parameters comprise transmit waveform, ratio of transmit to receive beamformed lines, imaging steering angle, receive line density, number of focal zones, location of focal zones, quadrature bandpass filter type and coefficients, compression curve, and speckle reduction parameters, among others. Because imaging parameters are typically selected to produce best overall image quality, the visualization quality of individual objects within the volume being imaged may be compromised. However, from the clinical standpoint it is beneficial that a single ultrasound image is presented to a clinician where there is high quality visualization of all objects of interest, including different biological structures and man-made objects.

Figure 1B:
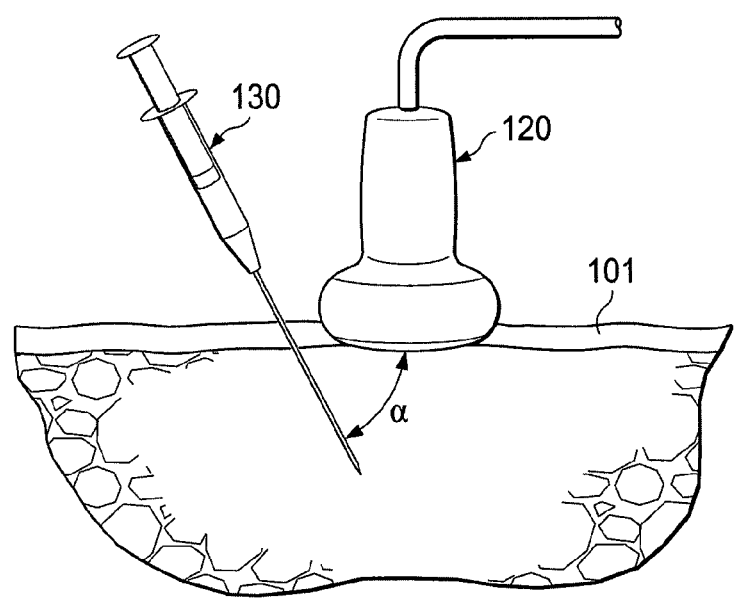

An exemplary case illustrating this problem is the visualization of instruments, such as interventional instrument 130 comprising needles, catheters, etc. when inserted at relatively steep angles relative to transducer 120 (as depicted in FIG. 1B). For example, a portion of interventional instrument 130, such as may comprise a needle, a catheter, a stent, a percutaneous tool, etc., is inserted into volume being imaged 101, to perform an interventional procedure. Exemplary procedures might require injecting pharmaceuticals into target 102, performing a biopsy with respect to target 102, etc. Typically, when the insertion angle (represented by angle α in FIG. 1B) is approximately 20° or greater, it is considered to be a steep angle of insertion.

When interventional instruments are inserted at steep angles, the imaging steering angles of the sub-frames configured for imaging target 102 may not provide satisfactory imaging of interventional instrument 130. For example, the effects of specular reflection may cause the signal reflected from the interventional instrument to not be readily visible in the resultant image. The failure to provide satisfactory imaging with respect to interventional instrument 130 is particularly problematic where ultrasound system 100 is being used to generate images to facilitate a clinician's performance of an interventional procedure using interventional instrument 130.

Although it might appear that the foregoing spatial compounding technique may be easily modified to include one or more sub-frames configured for imaging interventional instrument 130, the various different imaging signal steering angles of the sub-frames which may be compounded using spatial compounding techniques is not without restriction if image quality is to be maintained or improved. For example, it has been discovered that the use of sub-frames implementing more acute steering angles (e.g., in excess of ±15° as may be desirable for use in imaging an interventional instrument inserted at a steep angle) in combination with the sub-frames of the foregoing imaging signature implementing less acute steering angles results in image degradation. That is, particular sub-frames are not compatible for generation of a frame using spatial compounding techniques because their compounding results in undesired or unacceptable image clutter, artifacts, etc. By "compatible," as used with reference to imaging parameters, it is meant that various imaging parameters (e.g., optimized or otherwise configured for use with respect to a particular object) may be used together (e.g., in a spatial compounding technique) without resulting in undesired or unacceptable image clutter, artifacts, etc. Conversely, by "not compatible" it is meant that imaging parameters (e.g., optimized or otherwise configured for use with respect to a particular object) may result in undesired or unacceptable image clutter, artifacts, etc. when used with respect to other imaging parameters (e.g., optimized or otherwise configured for use with other objects) and thus may be considered not to be compatible with such other imaging parameters.

In order to achieve high quality ultrasound visualization of particular objects within an imaged volume, embodiments of the present invention employ ultrasound imaging signatures which comprise one or more ultrasound imaging parameter values tailored to produce high quality ultrasound visualization of particular objects of interest. Such ultrasound imaging signatures comprise imaging parameters associated with either the acquisition and/or the processing of ultrasound data such that the parameter values are tailored to the high quality ultrasound visualization of a particular object of interest. In a preferred embodiment, a particular ultrasound imaging signature is defined for an object of interest without compromise in favor of the visualization of other objects being scanned.

According to embodiments of the present invention, the particular sub-frames utilized in generating a frame are selected so as to be optimized or otherwise configured for imaging particular objects according to the ultrasound imaging signature defined for a particular object. For example, such a collection of sub-frames may be configured for providing relatively high quality images with respect to subsurface regions of living tissue (e.g., general patient anatomy), particular tissue (e.g., heart, liver, uterus, stomach, etc.), particular structure (e.g., bone joints, artery bifurcation, nerve cluster, etc.), or man-made objects such as implants and instruments, and/or the like. According to embodiments of the present invention, the collection and processing of sub-frames, e.g., sub-frames 201-203, and their combination to produce a frame, e.g., frame 200, is associated with an ultrasound imaging signature associated with target 102.

Therefore, embodiments of the ultrasound imaging system of the present invention are operable to implement a plurality of different ultrasound imaging signatures wherein each ultrasound imaging signature of the plurality of imaging signatures implemented provides high quality visualization of a corresponding object of interest within a scanned volume. According to an embodiment of the invention, a first ultrasound imaging signature (e.g., comprising sub-frames 201-203 of FIGS. 2A-2C) is configured for providing relatively high quality images with respect to subsurface regions of volume being imaged 101. Correspondingly, a second ultrasound imaging signature (e.g., comprising sub-frames 301-302 of FIGS. 3A-3B) is configured for providing relatively high quality images with respect to a portion of interventional instrument 130 inserted at a steep angle into volume being imaged 101.

Figure 3A:
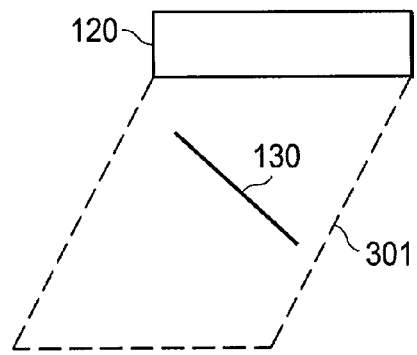
FIGS. 3A and 3B show different sub-frames according to an embodiment of the invention.
Figure 3B:
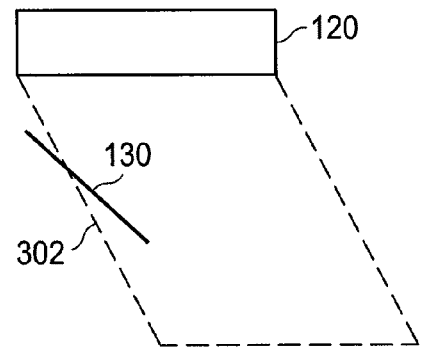
Figure 3C:
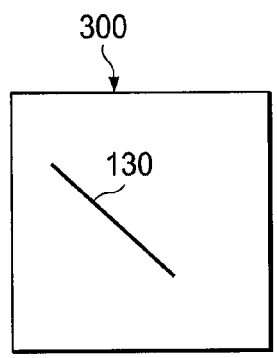
FIG. 3C shows a frame generated using the sub-frames of the ultrasound imaging signature of FIGS. 3A and 3B according to an embodiment of the invention.
Figure 4:
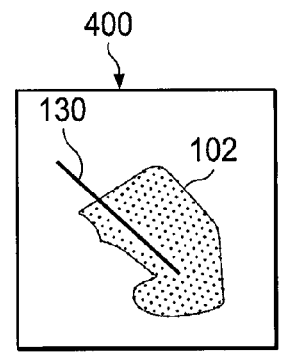
FIG. 4 shows a final ultrasound image generated using the frames of FIGS. 2D and 3C according to an embodiment of the invention.

Sub-frames 301 and 302 of FIGS. 3A and 3B are configured for providing relatively high quality images with respect to interventional instrument 130, inserted at a steep angle, by implementing more acute steering angles to provide imaging data which reduces specular reflection disadvantages associated with interventional instrument 130. As has been discussed, interventional instrument 130 of the illustrated embodiment has a relatively steep angle with respect to the face of transducer 120 and is visible in frame 300 of FIG. 3C because the steering angles of at least one of sub-frames 301 and 302 is highly steered in one or more appropriate directions. It should be appreciated that, for clarity, artifacts from item to be imaged 101 (e.g., tissue and other structure) are not shown in sub-frame 300. Features of item to be imaged 101 would be highly degraded due to clutter and other factors associated with the use of sub-frames 301 and 302.

In configuring sub-frames 301 and 302 according to embodiments of the invention, the steering angles may be selected to substantially correspond to the insertion angle of interventional instrument 130 so as to provide transmission of signals more normal to the surface of interventional instrument 130. By way of example, interventional instrument 130 may be inserted at an angle of approximately 60° and correspondingly the steering angles implemented with respect to sub-frames 301 and 302 may be ±30° so as to provide transmission of acoustic waves which result in approximately a 90° angle of incidence with a face of interventional instrument 130. It should be appreciated that other angles of incidence, other than 90°, may be utilized according to embodiments of the invention. Preferred embodiments operate to facilitate angles of incidence in the range of 75° degrees to 105° degrees with respect to a surface of an object for providing high quality images of the object.

It should be appreciated that the insertion angle of an interventional instrument being imaged may be known or assumed for configuring and/or selecting the parameter values for an appropriate imaging signature for use therewith by a number of means. For example, an interventional instrument guide may be utilized which provides for a particular angle of insertion. The angle of insertion provided by a selected interventional instrument guide may be provided automatically to a processor of system unit 110 using various sensor or other feedback techniques, such as those shown in U.S. patent application Ser. No. 11/216,735 entitled "Medical Device Guide Locator," filed Aug. 31, 2005, assigned to Sonosite, Inc. the assignee of the present invention, the disclosure of which is hereby incorporated herein by reference. Where an interventional instrument is inserted free-hand (e.g., without the aid of a guide), an insertion angle used for configuration and/or selection of an appropriate imaging signature may be estimated as the intended insertion angle, a typical insertion angle, a calculated insertion angle, etc. Additionally or alternatively, an insertion angle may be determined through analysis of collected data (e.g., imaging data), such as through identifying attributes of an interventional instrument within a generated image.

The ultrasound imaging signatures utilized in generating the final image may have differing numbers and types of imaging parameters. For example, the first of the foregoing exemplary imaging signatures comprises 3 sub-frames while the second of the foregoing exemplary imaging signatures comprises 2 sub-frames. There is no limitation regarding the illustrative number of sub-frames or other imaging parameters and thus imaging signatures of embodiments may implement fewer or more sub-frames than that illustrated. For example, an imaging signature configured for use with respect to a particular object or feature, such as an ultrasound imaging signature configured for use with respect to interventional instrument 130, may implement a single sub-frame according to embodiments of the invention.

Although embodiments of ultrasound imaging signatures comprising sub-frames implementing various steering angles, embodiments of the invention may utilize ultrasound imaging signatures comprising various additional or alternative imaging parameters. For example, ultrasound imaging signatures of embodiments may provide specification configurations of imaging parameters which include transmit waveforms, ratio of transmit to receive beamformed lines, steering angle, receive line density, number of focal zones, location of focal zones, quadrature bandpass filter type and coefficients, compression curve, speckle reduction parameters, etc. to enhance the particular objects of interest.

Figure 5:
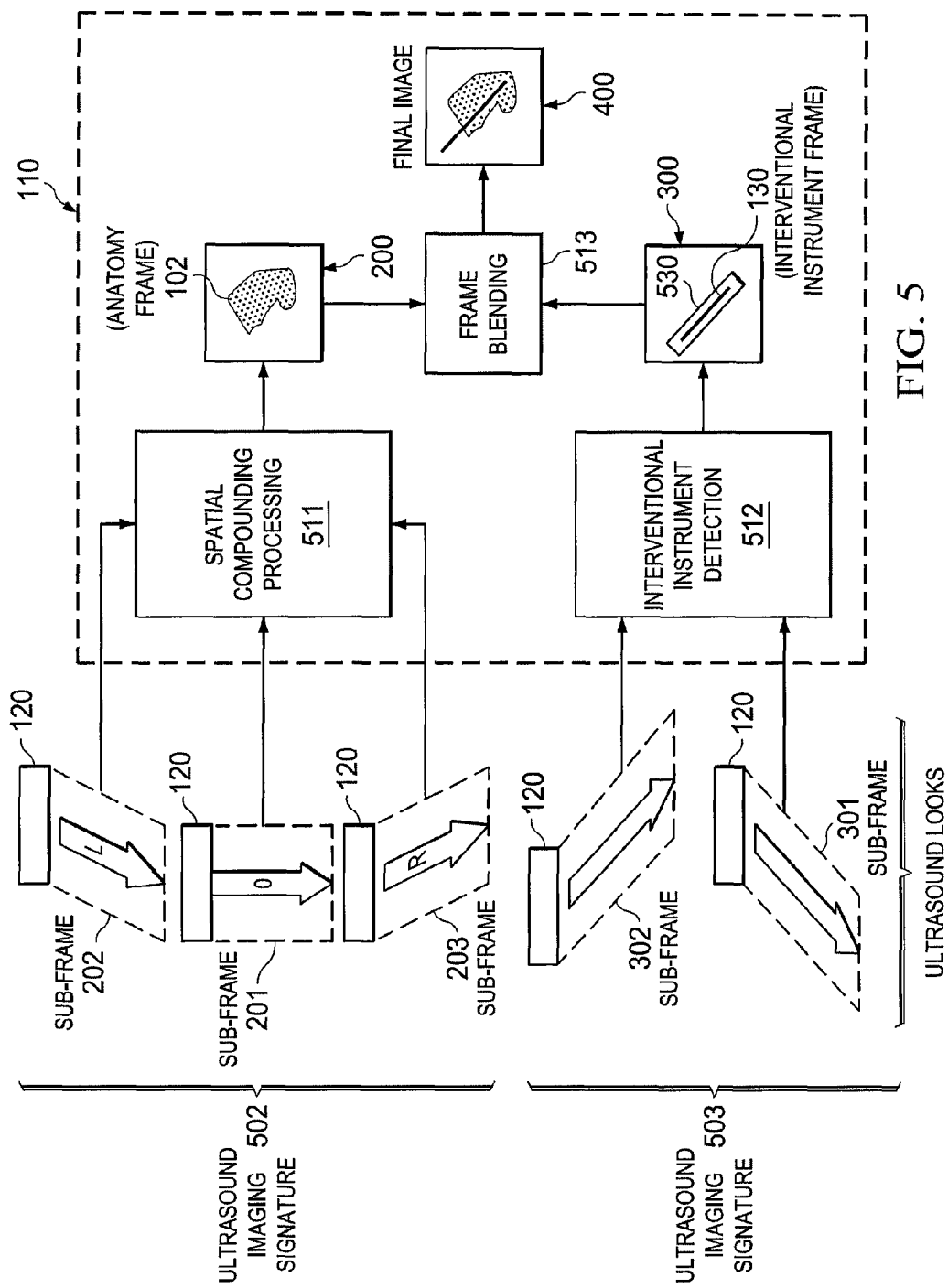
FIG. 5 shows a schematic diagram of operation of the ultrasound imaging system of FIGS. 1A and 1B operating to generate a final ultrasound image using a multiple ultrasound imaging signature technique of an embodiment of the invention.
Figure 6:
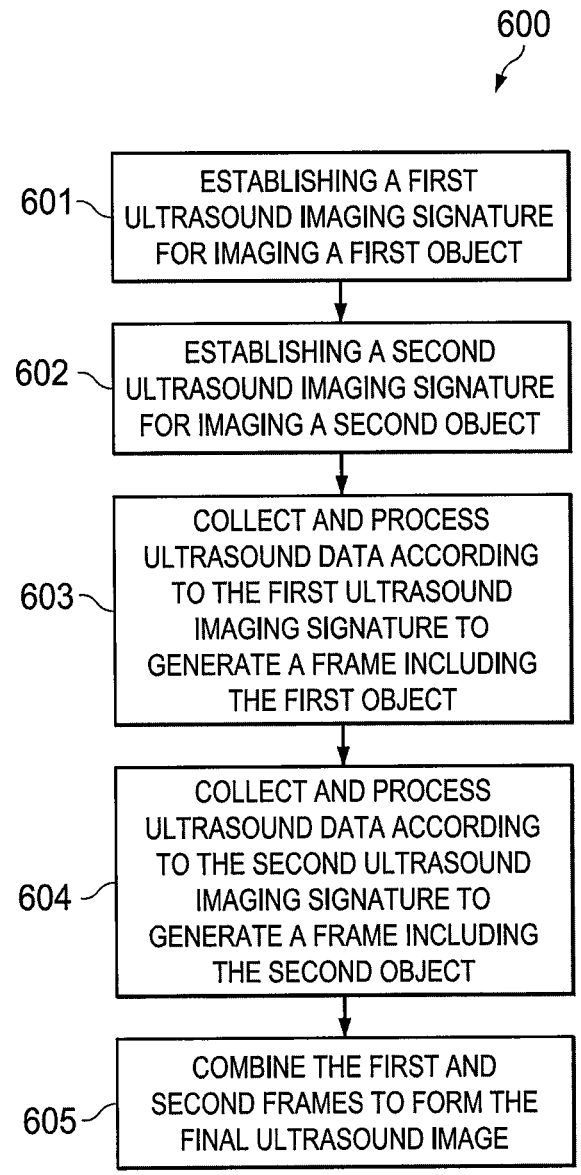
FIG. 6 shows a high level flow diagram of operation of the ultrasound imaging system of FIGS. 1A and 1B operating to generate a final ultrasound image using a multiple ultrasound imaging signature technique of an embodiment of the invention.

Irrespective of the particular ultrasound imaging signatures used, system unit 110 of embodiments operates to generate image frames (e.g., frames 200 of FIGS. 2D and 300 of FIG. 3C) using signals received and processed with respect to each of the ultrasound imaging signatures invoked. Such image frames formed according to embodiments are preferably combined or blended to form a final image. FIGS. 5 and 6 illustrate operation of ultrasound system 100 in generating final image 400 using a plurality of imaging signatures, and image frames generated there from, as described herein.

As shown in block diagram 600 of the embodiment illustrated in FIG. 6, a first ultrasound imaging signature for imaging a first object (e.g., object 102) is established at block 601. For example, ultrasound imaging signature 502 of FIG. 5 (comprising sub-frames 201-203) may be established for use in imaging a first object. Additionally, a second ultrasound imaging signature for imaging a second object (e.g., interventional instrument 130) is established at block 602 of the illustrated embodiment. For example, ultrasound imaging signature 503 of FIG. 5 (comprising sub-frames 301-302) may be established for use in imaging a second object.

At block 603 of the illustrated embodiment imaging data is collected and processed using the first ultrasound imaging signature. For example, system unit 110 and transducer 120 may cooperate to implement the first ultrasound imaging signature and collect and process imaging data. Additionally, at block 604 of the illustrated embodiment imaging data is collected and processed using the second ultrasound imaging signature. For example, system unit 110 and transducer 120 may cooperate to implement the second ultrasound imaging signature and collect and process imaging data.

As shown in the embodiment of FIG. 5, data collected by transducer 120 operating in accordance with ultrasound imaging signature 502 is provided to system unit 110. The sub-frames collected and processed using the first imaging signature are further processed by system unit 110 to provide a frame including the first object at block 603 of the illustrated embodiment. For example, spatial compounding processing 511 of embodiments, as may comprise a processor operating under control of an instruction set defining operation as described herein, is operable with respect to the data collected using ultrasound imaging signature 502 to generate frame 200 comprising a high quality image of target 102.

Correspondingly, data collected by transducer 120 operating in accordance with ultrasound imaging signature 503 is provided to system unit 110. The sub-frames collected and processed using the second ultrasound imaging signature are further processed by system unit 110 to provide a frame including the second object at block 604 of the illustrated embodiment. For example, interventional instrument detection 512, as may be provided by algorithms operable upon a processor of system unit 110, is operable with respect to the data collected using ultrasound imaging signature 503 to generate frame 300 comprising a high quality image of a portion of interventional instrument 130.

Interventional instrument detection 512 of embodiments, as may comprise a processor operating under control of an instruction set defining operation as described herein, provides operation to detect interventional instrument 130 or other objects of interest. For example, algorithms of interventional instrument detection 512 may analyze data collected by transducer 120 to identify attributes of interventional instrument 130 therein for configuration and/or selection of a particular ultrasound imaging signature for use in providing a high quality image thereof. Additionally or alternatively, embodiments of interventional instrument detection 512 operate to identify interventional instrument 130 within one or more sub-frames, e.g., sub-frames 301 and 302, to provide isolation of the interventional instrument for generation of frame 300 where the interventional instrument and its surrounding areas are shown. For example, the shape or other characteristics of interventional instrument 130 may be known (e.g., an interventional instrument in the form of a needle has a known shape, e.g., a linear segment) and may be readily identified by using an appropriate algorithm. In one embodiment, the mathematical framework of the Hough Transform is used to detect the interventional instrument. This is a well known framework for detecting lines and any curve that can be expressed in a parametric form. Using this approach the object of interest can be modeled as a straight line or a parametric curve and the algorithm would determine where the object is within a sub-frame, e.g., sub-frames 301 and 302.

Irrespective of the particular technique implemented, operation of interventional instrument detection 512 of embodiments provides a segmentation of the interventional instrument 130 and its immediate surrounding area, the result of which is mask 530. The segmentation result, e.g., mask 530, enables the isolated use of interventional instrument 530 and its surrounding area in generating the final image 400 without degrading the tissue image (e.g., as may be provided by frame 102).

Figure 7:
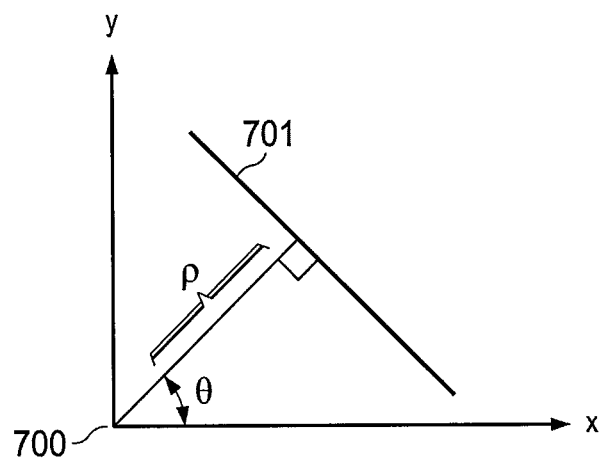
FIG. 7 shows a coordinate system for detecting straight lines in sub-frames according to embodiments of the invention.

As previously mentioned, the Hough Transform for detecting straight lines is used with sub-frames 301 and 302 according to embodiments. According to one implementation of the Hough Transform and directing attention to FIG. 7, line 701 in coordinate system 700 $\{x,y\}$, can be expressed by the equation:

$$\rho = x \cdot \cos\theta + y \cdot \sin\theta \quad (1)$$

where $\rho$ is the distance of the line from the origin of coordinate system 700 $\{x,y\}$ and $\theta$ is the angle between a line that is perpendicular to the line of interest 701 and the axis x of the coordinate system $\{x,y\}$. During an initialization process of the Hough Transform according to embodiments a 2D array that contains the sub-frame pixels in the coordinate system $\{x,y\}$, and a second 2D array called the accumulator array are defined. Each cell in the accumulator array corresponds to a particular set of parameters $(\rho_0, \theta_0)$ which represent a single line in the processed sub-frame, as shown by equation (1). The size of the 2D accumulator array depends on the range of shortest distances $\rho$ and angles $\theta$ that are of interest and the resolution by which they need to be defined. Once initialization is complete, the main mechanism of the Hough Transform is to sequence through all the pixels of a sub-frame and for each pixel $(x_0, y_0)$ that satisfies a set of criteria, such as intensity threshold, gradient strength etc., a counter is increased in the accumulator array for all the cells $(\rho, \theta)$ that satisfy equation (1) for the pixel $(x_0, y_0)$. In operation according to embodiments, after the entire sub-frame is sequenced the cell in the accumulator array with the highest counter value corresponds to the 2D line in the image sub-frames 301 or 302 representing the interventional instrument.

To further identify the particular segment along the 2D line where the interventional instrument is located, the intensity and gradient magnitude, along the perpendicular direction to the detected line, are examined for each pixel along the 2D line identified in the sub-frame according to embodiments. The pixels along the detected 2D line for which both the aforementioned intensity and gradient magnitude exceed a certain threshold define the particular location of the interventional instrument along the 2D line detected in the sub-frame and can be used to define mask 530 in frame 300 shown in FIG. 5 (e.g., a margin, such as a margin of a predetermined number of pixels, a predetermined distance, a percentage of the object's size, etc., may be used around the object to define the mask). According to one embodiment interventional instrument detection 512 can include a preprocessing step for removing sub-frame artifacts and noise, before the Hough Transform or other object identification technique is applied.

It should be appreciated that, although shown as being separate in the illustrated embodiment, spatial compounding processing 511 and interventional instrument detection 512 may be provided in combined circuitry according to embodiments. For example, a same processor may operate under control of an instruction set defining operation of spatial compounding processing 511 and an instruction set defining operation of interventional instrument detection 512, if desired.

Having generated frames 200 and 300, each providing a high quality image with respect to different objects of area to be imaged 101, system unit 110 of the illustrated embodiment utilizes frame blending 513 to blend frames 200 and 300 to form final image 400 providing a high quality image of various objects within volume being imaged 101 at block 605. For example, mask 530 of frame 300 defining the appropriate location for interventional instrument 130 may be blended into frame 200 to form final image 400. In the illustrated embodiment frames 200 and 300 are aligned based on the acquisition and processing used to generate them, whereas mask 530 serves as a means to identify the portion of frame 300 that will be blended with frame 200. For pixels outside of the region identified by mask 530 the value of the pixels in final image 400 are identical to those of frame 200 according to embodiments. For each pixel location within mask 530 the resulting pixel value for final image 400 may be a combination of the corresponding pixel values found in frames 200 and 300.

A blending function may be implemented by frame blending 513 to provide the foregoing blending of frames to generate a final image. Assuming that a pixel $(x_0, y_0)$ is within the region identified by mask 530 and that $f_1(x_0, y_0)$, $f_2(x_0, y_0)$, and $f(x_0, y_0)$, are the pixel values of frames 200, 300 and final image 400 respectively, we can write the following blending function equation:

$$f(x_0, y_0) = (1-b) * f_1(x_0, y_0) + *f_2(x_0, y_0) \quad (2)$$

where b is a coefficient between 0 and 1 that can be constant, e.g., 0.5 to produce an average of the two pixel values. In another embodiment coefficient b can be a function of the location within the mask where coefficient b shall have higher values for locations in mask 530 closer to interventional instrument 130, and lower values for locations in mask 530 farther from the interventional instrument 530. Alternatively, instead of applying a linear operation shown by equation (2), a non-linear operation can be used in a blending function of embodiments. In one example of such a case, $f(x_0, y_0)$ can be the maximum of values $f_1(x_0, y_0)$ and $f_2(x_0, y_0)$.

While only two ultrasound imaging signatures are shown with respect to the illustrated embodiment, it should be appreciated that any number of ultrasound imaging signatures can be used as appropriate to particular embodiments. For example, where 3 objects of interest (e.g., a nerve, an interventional instrument, and a main or underlying volume) are to be imaged, embodiments may implement 3 ultrasound imaging signatures (e.g., configured for a corresponding one of the nerve, interventional instrument, and main volume) may be used to generate sub-frames blended to form a frame.

Through frame generation and blending according to embodiments of the invention, a final image is generated which provides a high quality image of the objects, substantially free of undesired or unacceptable image clutter, artifacts, etc., when using imaging parameters which are otherwise not compatible. For example, using an ultrasound imaging signature frame technique of embodiments of the invention, imaging is not degraded although image processing is performed to render an interventional instrument which is inserted at a steep angle clearly visible in the resulting image.

Operation of system unit 110 according to embodiments may provide image processing in addition to the foregoing spatial compounding, interventional instrument detection, and frame blending. For example, embodiments of the invention may provide speckle reduction and/or other types of image processing algorithms with respect to frames and/or final image.

Figure 8:
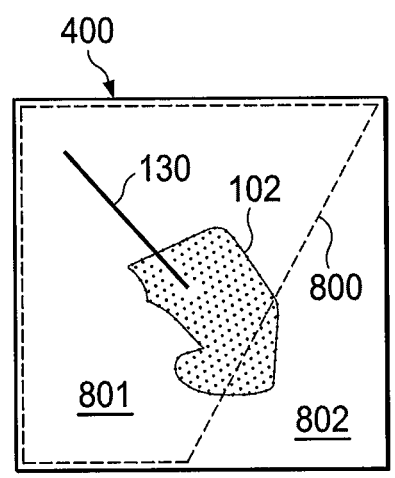
FIG. 8 shows graphics in a final image to indicate the coverage area defined by the highly steered sub-frame of embodiments of the invention.

Additionally or alternatively, directing attention to FIG. 8, operation of system 110 of embodiments includes graphics 800 (shown here as a trapezoid indicated by dashed lines) in final image 400, such as to indicate the coverage area 801. Graphics 800 may be controlled, for example, by parameters used to generate frame 300, to indicate coverage area 801 defined by the highly steered sub-frame 301 in FIG. 5. Coverage area 801, as indicated by graphics 800, comprises an area where high quality visualization of the interventional instrument is enabled. Such graphics allow the clinician or other operator to know that items of interest will only appear with high quality visualization in certain portions, e.g., coverage area 801, of the final image and if they do not, e.g. if they appear in region 802 of the final image 400, then care should be used because the object (such as the interventional instrument) is out of the high quality visualization field of view (although the interventional instrument may still be within the volume being imaged).

If desired, certain attributes (such as the end point, the mid point, etc.) of the interventional instrument or other target could be coded so that different portions show up differently in the final image (e.g., different intensities, color, etc.), such as to alert the clinician or other operator as to which portion of an object (e.g., the interventional instrument) is being overlaid. Such image processing may be provided by frame blending 513 of embodiments, for example.

It should be appreciated that application of an ultrasound multi-imaging signature technique of embodiments of the invention is not limited to use with interventional instruments. For example, an ultrasound imaging signature may be configured to image a nerve, while another ultrasound imaging signature is configured to image another object, such as a tumor, whereby these ultrasound imaging signatures are used in cooperation to form frames which are blended to provide a final image showing a high quality image of each such object.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for operating an ultrasound machine to produce an ultrasound image including an image of an interventional instrument, comprising:
    establishing a first ultrasound imaging signature having one or more imaging parameters including a transmit waveform, ratio of transmit to receive beamformed lines, imaging steering angle, receive line density, number of focal zones, quadrature bypass filter type and coefficients, compression curve and speckle reduction parameters selected to produce a high quality image of tissue within a volume to be imaged;
    establishing a second ultrasound imaging signature having one or more imaging parameters including a transmit waveform, ratio of transmit to receive beamformed lines, imaging steering angle, receive line density, number of focal zones, quadrature bypass filter type and coefficients, compression curve and speckle reduction parameters selected to produce a high quality image of an instrument within the volume to be imaged;
    generating a first frame using the image data resulting from application of the first ultrasound imaging signature; and
    generating a second frame using the image data resulting from application of the second ultrasound imaging signature;
    detecting pixels in the second frame that correspond to the interventional instrument;
    automatically determining a mask of pixels that correspond to the location of the interventional instrument;
    blending pixels from the first frame and the second frame in a region that is inside the mask and using pixels from the first frame in a region that is outside the mask to form a blended final ultrasound image; and
    producing a graphic indication on the blended final ultrasound image that indicates the boundaries of a coverage area in the blended final ultrasound image where one or more of the imaging parameters of the second ultrasound imaging signature is selected to produce a high quality image of the interventional instrument.

2. The method of claim 1, wherein the interventional instrument is selected from the group consisting of a needle, a catheter, a stent, and a percutaneous tool.

3. The method of claim 1, wherein the imaging steering angle of the first ultrasound imaging signature is selected to provide imaging of the tissue at a desired quality and the imaging steering angle of the second ultrasound imaging signature is selected to provide imaging of the interventional instrument at a desired quality.

4. The method of claim 3, wherein the imaging steering angle of the second ultrasound imaging signature is more acute than the imaging steering angle of the first ultrasound imaging signature.

5. The method of claim 4, wherein the imaging steering angle of the first ultrasound imaging signature comprises a steering angle magnitude under plus or minus 20 degrees and wherein the imaging steering angle of the second ultrasound imaging signature comprises a steering angle magnitude greater than plus or minus 20 degrees.

6. An imaging system comprising:
an ultrasound imaging system configured to produce:
  a first frame from one or more subframes that are acquired with a first imaging signature having one or more imaging parameters including a transmit waveform, ratio of transmit to receive beamformed lines, imaging steering angle, receive line density, number of focal zones, quadrature bypass filter type and coefficients, compression curve and speckle reduction parameters selected to produce an image of tissue within a volume to be imaged; and
  a second frame from one or more subframes that are acquired with a second imaging signature having one or more imaging parameters including a transmit waveform, ratio of transmit to receive beamformed lines, imaging steering angle, receive line density, number of focal zones, quadrature bypass filter type and coefficients, compression curve and speckle reduction parameters selected to produce image of an interventional instrument within the volume to be imaged; and a processor in the ultrasound system that is configured to—
  detect pixels in the second frame that correspond to the interventional instrument;
  determine a mask of pixel coordinates that correspond to the location of the interventional instrument, wherein the mask is defined by a region in the second frame that includes the detected pixels corresponding to the interventional instrument and a number of pixels immediately surrounding the detected pixels; and
  combine a first set of pixels from the first frame and a second set of pixels from the second frame in an area corresponding to the mask and using pixels from the first frame in an area outside the mask to form a blended final ultrasound image comprising the tissue and the interventional instrument; and
  producing a graphic on the blended final ultrasound image that indicates the boundaries of a coverage area in the blended final ultrasound image where one of more of the imaging parameters of the second ultrasound imaging signature is selected to produce the image of the interventional instrument.

7. The system of claim 6, wherein the interventional instrument is selected from the group consisting of a needle, a catheter, a stent, and a percutaneous tool.

8. The system of claim 6, wherein the imaging signal steering angle of at least one of the first and second imaging signature is determined during operation of the system.

9. The system of claim 6, wherein the imaging steering angle of the second imaging signature is more acute than the imaging steering angle of the first imaging signature.

10. The system of claim 9, wherein the imaging steering angle of the first imaging signature comprises a steering angle magnitude under plus or minus 20 degrees and wherein the imaging steering angle of the second imaging signature comprises a steering angle magnitude greater than plus or minus 20 degrees.

* * * * *

UNITED STATES PATENT AND TRADEMARK OFFICE
CERTIFICATE OF CORRECTION

PATENT NO. : 8,861,822 B2  
APPLICATION NO. : 12/790109  
DATED : October 14, 2014  
INVENTOR(S) : Pagoulatos et al.

Page 1 of 1

Figure 2A:
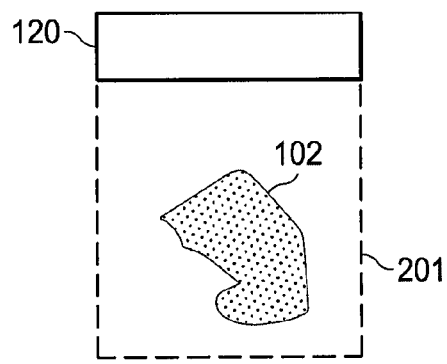
FIGS. 2A-2C show different sub-frames utilized according to an embodiment of the invention.
Figure 2B:
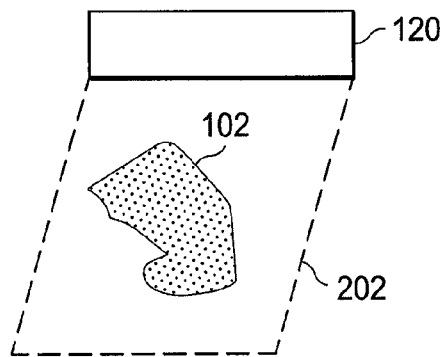
Figure 2C:
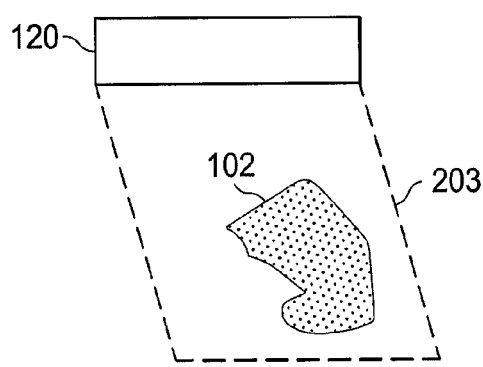
Figure 2D:
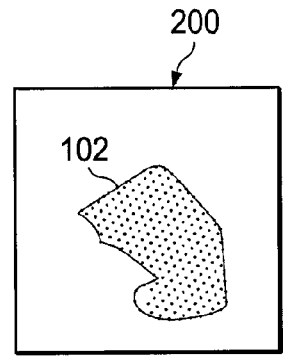
FIG. 2D shows a frame generated from sub-frames of FIGS. 2A-2C according to an embodiment of the invention.

It is certified that error appears in the above-identified patent and that said Letters Patent is hereby corrected as shown below:

In the Specification:

At column 8, line number 25, delete "FIGS. 2D" and insert --FIG. 2D--;

In the Claims:

At column 12, claim number 1, line number 34, delete "bypass" and insert --bandpass--;

At column 12, claim number 1, line number 42, delete "bypass" and insert --bandpass--;

At column 13, claim number 6, line number 24, delete "bypass" and insert --bandpass--;

At column 13, claim number 6, line number 33, delete "bypass" and insert --bandpass--;

At column 13, claim number 6, line number 35, delete "produce image" and insert --produce an image--; and At column 14, claim number 6, line number 18, delete "one of" and insert --one or--.

Signed and Sealed this  
Eleventh Day of August, 2015

Michelle K. Lee  
*Director of the United States Patent and Trademark Office*